US010130517B2

(12) United States Patent
Gates

(10) Patent No.: US 10,130,517 B2
(45) Date of Patent: Nov. 20, 2018

(54) HEARING PROTECTION SYSTEMS

(71) Applicant: Craig D Gates, Mead, WA (US)

(72) Inventor: Craig D Gates, Mead, WA (US)

( * ) Notice: Subject to any disclaimer, the term of this patent is extended or adjusted under 35 U.S.C. 154(b) by 0 days.

(21) Appl. No.: 15/594,170

(22) Filed: May 12, 2017

(65) Prior Publication Data

US 2017/0252217 A1     Sep. 7, 2017

Related U.S. Application Data

(63) Continuation-in-part of application No. 15/058,575, filed on Mar. 2, 2016.

(51) Int. Cl.
| | | |
|---|---|---|
| A61F 11/06 | (2006.01) | |
| A42B 3/16 | (2006.01) | |
| H04R 1/10 | (2006.01) | |
| A61F 11/08 | (2006.01) | |
| F41C 27/00 | (2006.01) | |

(52) U.S. Cl.
CPC .............. *A61F 11/08* (2013.01); *F41C 27/00* (2013.01); *A61F 2011/085* (2013.01); *A61F 2250/0058* (2013.01)

(58) Field of Classification Search
CPC . A61F 11/12; A61F 11/14; A42B 3/16; A42B 3/163; A42B 3/166; A42B 1/06; A42B 1/068; H04R 1/008; H04R 1/1091; H04R 1/1083; H04R 2460/09; H04R 2460/11; A63B 71/10
See application file for complete search history.

(56) References Cited

U.S. PATENT DOCUMENTS

| | | |
|---|---|---|
| 2,889,555 A | 6/1959 | Stuart |
| 3,335,720 A | 8/1967 | Aileo |
| 5,135,007 A | 8/1992 | Lo |
| 6,259,796 B1 | 7/2001 | Lin |
| 6,826,287 B2 | 11/2004 | Myers |
| 8,061,473 B1 | 11/2011 | Kerr |
| 8,107,663 B2 | 1/2012 | Lin |
| 8,718,312 B2 | 5/2014 | Lin |
| 8,732,864 B2 | 5/2014 | Fountain et al. |
| 8,767,995 B2 | 7/2014 | Hwang |
| 8,873,791 B2 | 10/2014 | Yang |
| 9,510,079 B1* | 11/2016 | Pastorino ............. H04R 1/1008 |
| 9,521,480 B2 | 12/2016 | Bauman et al. |
| 2004/0125976 A1 | 7/2004 | Reneker |

(Continued)

OTHER PUBLICATIONS

Office action for U.S. Appl. No. 15/058,575, dated Jan. 12, 2017, Gates, "Hearing Protection Systems", 7 pages.

(Continued)

*Primary Examiner* — Edgardo San Martin
(74) *Attorney, Agent, or Firm* — Lee & Hayes, PLLC

(57) ABSTRACT

A hearing protection system including an earplug moveably displaceable in a plane covering an ear of a user from an open position to a closed position in response to a signal received from a trigger mechanism. When in the open position, the earplug is positioned adjacent to the ear of the user to allow the user to hear ambient sound at an unchanged volume. When in the closed position, the earplug is positioned over the ear of the user to at least partly block the ambient sound and allow the user to hear the ambient sound at a reduced volume that is less than the unchanged volume.

7 Claims, 7 Drawing Sheets

(56) References Cited

U.S. PATENT DOCUMENTS

| | | |
|---|---|---|
| 2005/0105755 A1 | 5/2005 | Yueh |
| 2007/0177753 A1 | 8/2007 | Weinans et al. |
| 2012/0207320 A1 | 8/2012 | Avital |
| 2014/0190494 A1 | 7/2014 | Ely |
| 2016/0150310 A1 | 5/2016 | Bakalos |
| 2016/0199228 A1 | 7/2016 | Haukap |
| 2017/0252218 A1 | 9/2017 | Gates |

OTHER PUBLICATIONS

Office action for U.S. Appl. No. 15/058,575, dated Jun. 19, 2017, Gates, "Hearing Protection Systems", 8 pages.

* cited by examiner

HEARING PROTECTION SYSTEMS

RELATED APPLICATIONS

This application claims priority to and is a continuation-in-part application of U.S. patent application Ser. No. 15/058,575, filed on Mar. 2, 2016, which is incorporated by reference herein.

BACKGROUND

Protecting a hearing of a person may be difficult in conditions where hearing protection is desired at a time of an event but not desired until the event. This is particularly true for shooters, where hearing protection is not desired until the firing of a firearm. For example, a hunter may desire hearing protection at the time of firing a firearm but the hearing protection is not desired until the firing of the firearm so that the hunter may hear ambient sound naturally and unchanged for better hunting.

A person may use a variety of hearing protection devices to protect the persons hearing, however each of the hearing protection devices have disadvantages. For example, earplugs may be used, however the earplugs remain stuck in the ears of a user even when the earplugs are not needed and thus prevent the person from hearing ambient sound. For example, a hunter may plug his ears with earplugs to protect his ears at a time of firing a firearm, but the earplugs prevent the hunter from hearing ambient sounds like a location of game, a location of a dog, or verbal communication from another hunter. In another example, noise cancelling earplugs may be used, however the noise cancelling earplugs do not allow the user to hear unchanged ambient sound. Instead, noise cancelling earplugs inject reproduced ambient sound into the ears which is not the same as hearing the ambient sound naturally. For example, the noise cancelling earplugs receive ambient sound and inject digitally reproduced sound into the ears of the user that is distorted and thus not the same as the natural ambient sounds. Moreover, the earplugs are uncomfortable to use because the earplugs prevent heat from dissipating from the ears, causing the ears to perspire and the user to overheat.

Accordingly there remains a need in the art for a hearing protection system, allowing the user to hear ambient sound naturally and more comfortably, until the hearing protection system is needed to protect the ears from a loud noise.

SUMMARY

Hearing protection systems are configured to protect a hearing of a user from a loud noise. Generally, the hearing protection systems include earplugs that are displaced between an open position and a closed position based on a position of a device. When in the open position, the earplugs are positioned away from the ears of the user to allow the user to hear ambient sound naturally at an unchanged volume, and when in the closed position, the earplugs are positioned proximal to the ears of the user to at least partly block the ambient sound and allow the user to hear the ambient sound at a reduced volume that is less than the unchanged volume. This summary is provided to introduce simplified concepts of hearing protection systems, which are further described below in the Detailed Description. This summary is not intended to identify essential features of the claimed subject matter, nor is it intended for use in determining the scope of the claimed subject matter.

In one example, a hearing protection system includes an earplug displaceable between an open position and a closed position, and a trigger mechanism to cause the earplug to displace between the open position and the closed position based at least in part on a position of a device.

In another example, a hearing protection system includes an earplug attachable proximate to an ear of a user. The hearing protection system also includes a trigger mechanism to cause the earplug to displace between an open position and a closed position based at least in part on a position of a device.

In another example, a hearing protection system includes an earplug displaceable between an open position and a closed position in response to a signal received from a trigger mechanism.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Overview

Figure 1:
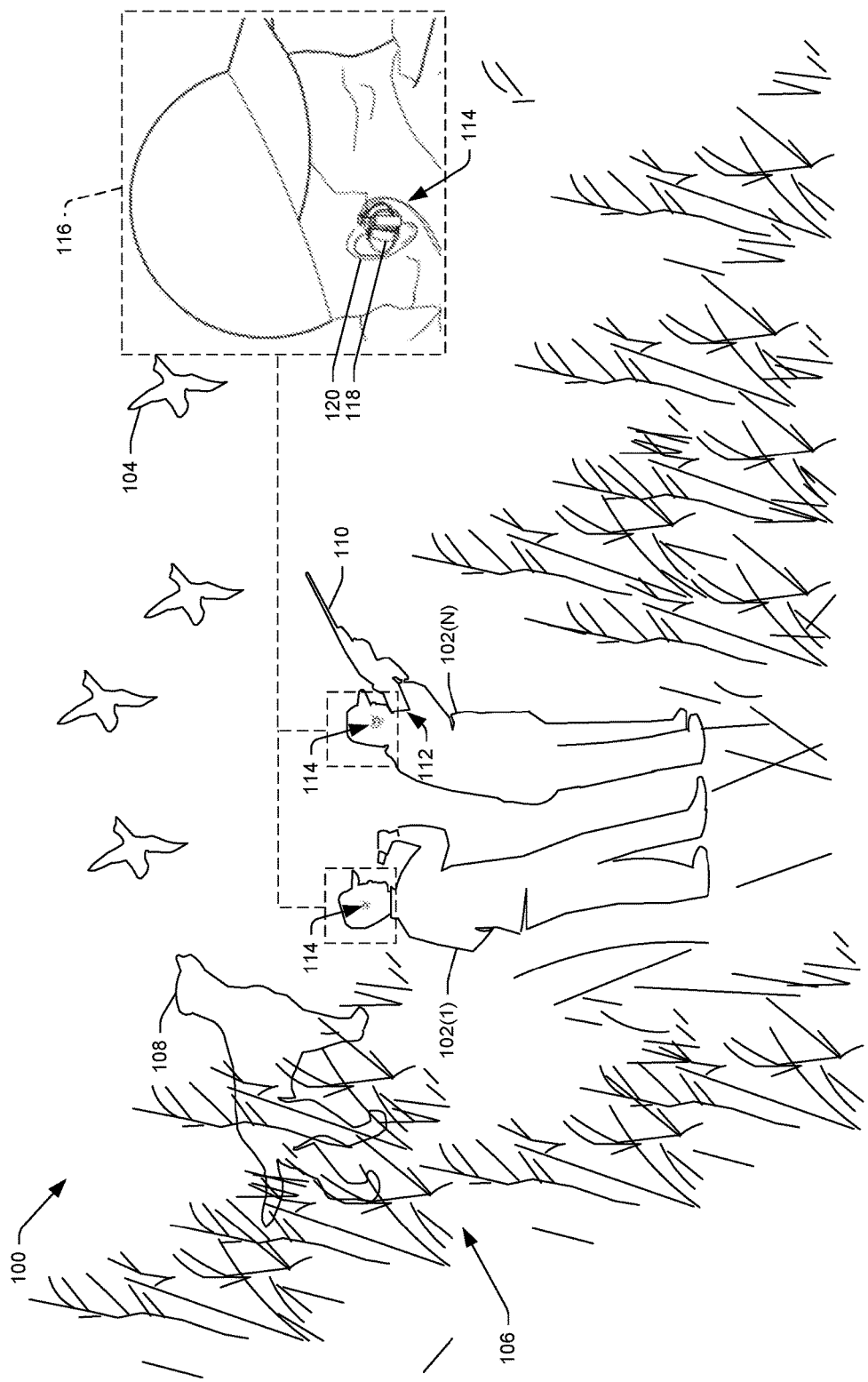
FIG. 1 illustrates an example hunting environment involving hunters.

This disclosure is directed to hearing protection systems that displace from an open position to a closed position to protect a person's hearing. For example, the hearing protection systems may include a trigger mechanism, responsive to movement of a device, to cause the hearing protection systems to displace from the open position to the closed position based at least in part on a position of the device. For example, the trigger mechanism may cause the hearing protection systems to displace to the closed position based on a position of a device relative to a portion of a body of a user. Stated otherwise, the trigger mechanism may base the closing criteria on a position of a firearm relative to a shoulder or a hand of a hunter. Moreover, the trigger mechanism may employ a sensor to continually sense the position of the firearm relative to the shoulder or the hand of the hunter. The trigger mechanism may cause the hearing protection systems to displace to the closed position where the hearing protection systems are positioned proximal to the ears of the hunter. In this way, the hearing protection systems at least partly close the ears of the hunter when the firearm is fired to prevent injury to the ears of the hunter. While this application describes various embodiments of hearing protection systems used in the field of hunting, this is by way of example and not limitation. For example, the hearing protection systems may be used in other fields such as military applications, construction applications, industrial applications, heavy equipment operation applications, machinery operation applications, music industry applications, aviation industry applications, etc.

The hearing protection systems may include an earplug displaceable between an open position and a closed position. For example, the earplug may be displaced from the open position, where the earplug is positioned away from an ear of a user to allow the user to hear ambient sound at an unchanged volume, to the closed position, where the earplug is positioned proximal to the ear of the user to at least partly block the ambient sound and allow the user to hear the ambient sound at a reduced volume that is less than the unchanged volume. A reduced volume as used herein comprises a noise reduction rating (NRR) of at least about 10 decibels to at most about 35 decibels. In the example where the hearing protection system includes a trigger mechanism employing a sensor to continually sense the position of a firearm relative to a shoulder of the hunter, the trigger mechanism may cause the earplug to be displaced between the open position and the closed position based at least partly on a position of the end or butt of the stock of a long gun (e.g., shotgun, rifle, muskets, etc.) relative to the shoulder of the hunter. For example, the trigger mechanism may employ a sensor (a touch sensor, an electro-optical sensor, a magnetic proximity sensor, radio-frequency identification (RFID), etc.) arranged with the shoulder of the hunter. The sensor to detect the butt of the stock of the long gun in response to a proximity of the butt of the long gun to the sensor arranged with the shoulder. In the example where the hearing protection system includes a trigger mechanism employing a sensor to continually sense the position of a firearm relative to a hand of the hunter, the trigger mechanism may cause the earplug to be displaced between the open position and the closed position based at least in part on a position of a grip and/or a trigger of a handgun (e.g., a pistol, a revolver, a pistol revolver, a revolving pistol, etc.) relative to a finger and/or a palm of the hand of the hunter. The sensor to detect the grip and/or the trigger of the handgun in response to a proximity of the grip and/or trigger of the handgun to a sensor arranged with the finger and/or the palm of the hand of the hunter.

Further, the hearing protection system may include an earplug attachable proximate to an ear of a user. For example, the hearing protection system may include a receptacle receivable by the ear of the user, and the earplug may be displaceably attached to the receptacle. The earplug may be displaceably attached to the receptacle such that when in the closed position the earplug is removeably received by a cavity of the receptacle to at least partly seal the cavity of the receptacle and to at least partly block ambient sound and allow the user to hear the ambient sound at a reduced volume.

The hearing protection systems may include a motor coupled to the earplug. The motor being coupled to the earplug to displace the earplug between the open position and the closed position based at least in part on a signal received from the trigger mechanism. For example, the motor may receive a wired or a wireless signal from the trigger mechanism that causes the motor to displace the earplug between the open position and the closed portion.

Illustrative Hearing Protection Systems

FIG. 1 illustrates an example hunting environment 100 involving hunters 102(1) and 102(N). For example, FIG. 1 illustrates a hunting environment 100 of the hunters 102(1) and 102(N) attempting to shoot game 104 flushed out of tall grass 106 by a dog 108. Further, while attempting to shoot the game 104 with a firearm 110, a butt 112 of the firearm 110 is "braced" or forced onto the shoulder of the hunter 102(N) to fire the firearm 110 at the game 104. While FIG. 1 illustrates a hunting environment 100 where the butt 112 of the firearm 110 is braced into the shoulder of the hunter, other types of hunting environments may occur. For example, a hunting environment may occur where a grip of a handgun is grasped by a palm of a hand of the hunter, or trigger of a handgun is touched by a finger of a hand of the hunter. In most cases, the firearm 110 is positioned to fire at the game 104 relative to a portion of the body of the hunter. As a result of the firearm 110 being positioned to fire at the game 104, a hearing protection system 114 used by the hunters 102(1) and 102(N) are displaced from an open position to a closed position to protect the ears of the hunters 102(1) and 102(N) from the noise produced from firing the firearm 110.

Detail view 116 illustrates the hearing protection system 114 in more detail, and shows an earplug 118 of the hearing protection system 114 arranged with the ears 120 of the hunters 102(1) and 102(N). Detail view 116 illustrates the earplug 118 of the hearing protection system 114 arranged to protect the hearing of the hunters 102(1) and 102(N) from the noise produced from firing the firearm 110 at the game 104. For example, detail view 116 illustrates the earplug 118 of the hearing protection system 114 displaced from the open position to the closed position as a result of the firearm 110 being positioned to fire at the game 104.

When the hearing protection system 114 is in the open position, the earplugs 118 are positioned away from the ears 120 of the hunters 102(1) and 102(N) to allow the hunters 102(1) and 102(N) to hear ambient sound at an unchanged volume. For example, when in the open position, the earplugs 118 are positioned away from the ears 120 of the hunters 102(1) and 102(N) to allow the hunters 102(1) and 102(N) to hear, naturally in the hunting environment 100, the dog 108 moving in the tall grass 106, the game 104 being flushed out of the tall grass 106, and verbal communication between the hunters 102(1) and 102(N) until the firearm 110 is moved into position to fire at the game 104. Because the earplugs 118 are positioned away from the ears 120 of the hunters 102(1) and 102(N), until the firearm 110 is positioned to be fired, the hearing protection system 114 allows the hunters 102(1) and 102(N) to hear the ambient sound naturally at an unchanged volume making the hearing protection system 114 more efficient and safe to use than earplugs that block the ambient sound, and more efficient and safe to use than noise cancelling earplugs that inject reproduced ambient sound into the ears. Moreover, because the earplugs 118 are positioned away from the ears 120 of the hunters 102(1) and 102(N) until the firearm 110 is positioned to fire at the game 104, the earplugs 118 allow heat to dissipate from the ears 120, and thus do not cause the ears 120 to perspire or the hunters 102(1) and 102(N) to overheat, making the hearing protection system 114 more comfortable to use than the earplugs and the noise cancelling earplugs that remain stuck in the ears of a user even when the earplugs and the noise cancelling earplugs are not needed.

When the firearm 110 is positioned to fire at the game 104, the hearing protection system 114 is in the closed position and the earplugs 118 are positioned proximal to the ears 120 of the hunters 102(1) and 102(N) to at least partly block the ambient sound and allow for the hunters 102(1) and 102(N) to hear the ambient sound at a reduced volume (e.g., a noise reduction of at least about 10 decibels to at most about 35 decibels) that is less than the unchanged volume. For example, when the firearm 110 is positioned to fire at the game 104, the earplugs 118 may be positioned proximal to the ears 120 of the hunters 102(1) and 102(N) to reduce the firing noise of the firearm received by the ears 120 of the hunters 102(1) and 102(N) by at least about 10 decibels to at most about 35 decibels to protect the hearing of the ears 120 of the hunters 102(1) and 102(N).

While FIG. 1 illustrates the hearing protection systems 114 arranged in the ears 120 of the hunters 102(1) and 102(N), the hearing protection systems 114 may not be arranged in the ears 120. For example, the hearing protection system 114 may be arranged with a headband, a muff, a helmet, a hat, a cap, a stocking cap, eyewear, etc. arranged to fit on the head of the user and interface with the ears of the user. Moreover, while FIG. 1 illustrates the hearing protection systems 114 including earplugs 118 arranged to fit in the ears 120 of the hunters 102(1) and 102(N), the hearing protection system 114 may include ear muffs, ear cups, ear pads, etc. arranged to fit on and/or over the ears 120 of the user.

The hearing protection system 114 may use a trigger mechanism, responsive to movement of the firearm 110, to cause the earplugs to displace between the open position and the closed position based at least in part on a position of the firearm 110. For example, the trigger mechanism may include a sensor arranged with a portion of the body of the hunter, and the trigger mechanism, responsive to movement of the firearm 110, causes the earplug 118 to displace between the open position and the closed position based at least in part on the position of the firearm 110 relative to the portion of the body of the hunter. For example, a sensor may be arranged with a shoulder of the hunter 102(N) that detects the butt 112 of the firearm 110 in response to the butt 112 of the firearm 110 being at a position relative the shoulder of the hunter 102(N). If the position of the butt 112 of the firearm 110 is positioned close enough to the shoulder of the hunter 102(N), the trigger mechanism may displace the earplugs 118 of the hunters 102(1) and 102(N). For example, the sensor may be any device that measures the position of the butt 112 of the firearm 110 relative to the shoulder of the hunter 102(N), and converts that position to a wired or a wireless signal that controls a motor that displaces the earplugs 118 from the open position to the closed position. The sensor may be a touch sensor, an electro-optical sensor, a magnetic proximity sensor, etc. For example, a touch sensor, an electro-optical sensor, a magnetic proximity sensor, etc. may be arranged with the shoulder of the hunter 102(N) and/or the butt 112 of the firearm 110 that senses when the butt 112 of the firearm 110 is within a threshold distance to the shoulder of the hunter 102(N).

FIG. 1 illustrates the hearing protection systems 114 may be connected to one or more hunters 102(1) and 102(N). For example, the hearing protection systems 114 of the hunters 102(1) and 102(N) may be communicatively coupled via wireless interconnection. For example, the wireless interconnection interconnecting the hearing protection systems 114 of the hunters 102(1) and 102(N) may be a radio interconnection, an infrared interconnection, a Bluetooth interconnection, etc. In an example where the hearing protection system 114 of the hunter 102(N) is wirelessly interconnected to the hearing protection system 114 of the hunter 102(1), the hearing protection system 114 of the hunter 102(N) may signal the hearing protection system 114 of the hunter 102(1) to displace from the open position to the closed position to protect the hearing of the hunter 102(1) from the noise produced from the hunter 102(N) firing the firearm 110. For example, the hearing protection systems 114 may include a transmitter, transceiver, antenna, etc. arranged with the trigger mechanisms of the hearing protection systems 114. The trigger mechanism of the hearing protection system 114 of the hunter 102(N) may send a signal to the hearing protection system 114 of the hunter 102(1). When the trigger mechanism of the hearing protection system 114 of the hunter 102(N) responds to movement of the firearm 110, and causes the earplugs 118 of the hunter 102(N) to displace between the open position and the closed position based at least in part on the position of the firearm 110 relative to the portion of the body of the hunter 102(N), the hearing protection system 114 of the hunter 102(N) may send a signal to the trigger mechanism of the hearing protection system 114 of the hunter 102(1) to displace the earplugs 118 of the hunter 102(1) between the open position and the closed position.

Figure 2:
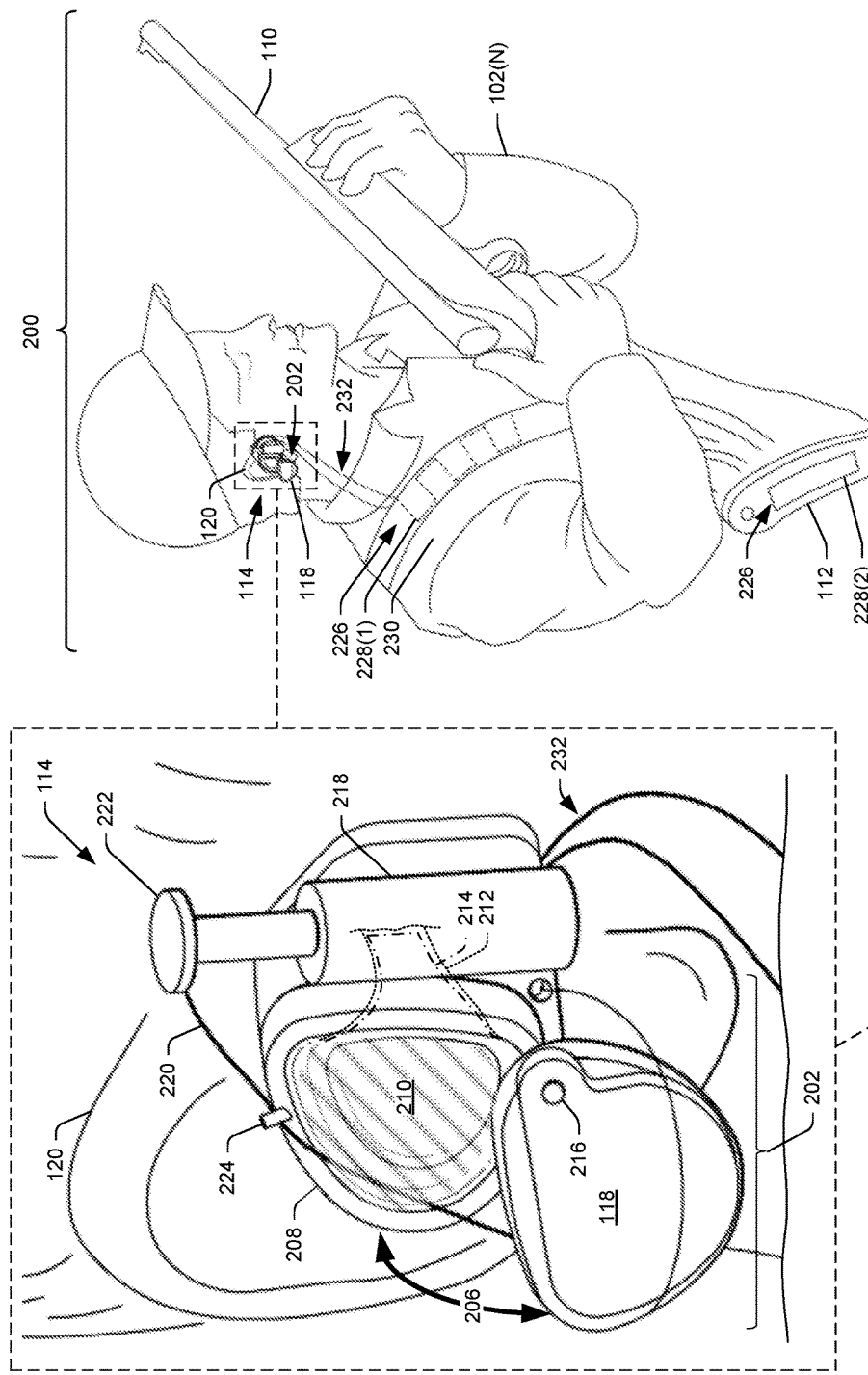
FIG. 2 illustrates a perspective view of an example hearing protection system in an open position that allows the hunters shown in FIG. 1 to hear ambient sound at an unchanged volume.

FIG. 2 illustrates a perspective view 200 of the example hearing protection system 114 shown in FIG. 1 in an open position 202 that allows the hunters 102(1) and 102(N) shown in FIG. 1 to hear ambient sound at an unchanged volume.

Detail view 204 illustrates the hearing protection system 114 in the open position 202 in more detail, and shows the earplug 118 positioned a distance 206 away from the ear 120 of the hunter 102(N) to allow the hunter 102(N) to hear ambient sound at an unchanged volume. The distance 206 the earplug 118 may be positioned away from the ear 120 may be at least about 0.06 inches (0.2 centimeters) to at most about 5 inches (13 centimeters).

Detail view 204 shows the hearing protection system 114 may include a receptacle 208. The receptacle 208 may be receivable by the ear 120. For example, the receptacle 208 may be a hollow earplug or hollow earpiece that may be received by the ear 120 of a user. The receptacle 208 may have a wall thickness of at least about 0.005 inches (0.01 centimeters) to at most about 0.02 inches (0.05 centimeters). The receptacle 208 may be formed of plastic, rubber, metal, wood, carbon fiber, fiberglass, glass, composite, etc. The receptacle 208 may include a cavity 210 arranged to fit in at least a portion of the ear 120. For example, the cavity 210 may be arranged in the receptacle 208 such that the cavity 210 interfaces with the inside the ear 120 proximate to the opening of the canal 212 (e.g., auditory canal) (illustrated as a hidden dashed line) of the ear 120. The receptacle 208 may include a channel 214 communicatively coupled to the cavity 210 and arranged to fit in at least a portion of the canal 212 of the ear 120.

Detail view 204 shows the earplug 118 is displaceably attached, via a hinge 216, to the receptacle 208. While detail view 204 shows the hinge 216 is rotatably attaching the earplug 118 to the receptacle 208, the hinge 216 may foldably, pivotably, slideably, etc. attach the earplug 118 to the receptacle 208. While detail view 204 shows the earplug 118 displaceably attached, via the hinge 216, to the receptacle 208, the earplug 118 may not be displaceably attached via the hinge 216. For example, the earplug 118 may be displaceably attached to the receptacle 208 via a hydraulic actuator, pneumatic actuator, magnetic actuator, etc. Further, while FIG. 2 illustrates the earplug 118 displaceably attached to the receptacle 208, the earplug 118 may not be displaceably attached to the receptacle 208. For example, the earplug 118 may be displaceably attached to a headband, a muff, a helmet, a hat, a cap, a stocking cap, eyewear, etc. arranged to fit on the head of the user.

Detail view 204 shows a motor 218 coupled to the earplug 118. For example, the motor 218 may be fixed to the receptacle 208 and coupled, via a member 220, to the earplug 118. The member 220 may be a line, wire, a chain, etc. having first end fixed to the earplug 118 and second end fixed to a rotating shaft 222 of the motor 218. When the motor 218 rotates the rotating shaft 222, the member 220 wraps around the rotating shaft 222. As the member 220 wraps around the rotating shaft 222, the member 220 displaces the earplug 118 from the open position 202 to the closed position (described in detail with regard to FIG. 3 below). Detail view 204 shows a guide member 224 fixed to the receptacle 208 and arranged to guide the member 220 as the member 220 is displaced via the rotating shaft 222. The guide member 224 may be a post, a hook, a ring, a ferrule, etc. arranged to guide the member 220 as the member 220 is displaced via the rotating shaft 222.

FIG. 2 illustrates a trigger mechanism 226 may have a first sensor 228(1) arranged with a shoulder 230 of the hunter 102(N) and a second sensor 228(2) arranged with the butt 112 of the firearm 110. The first and second sensors 228(1) and 228(2) measure the position of the butt 112 of the firearm 110 relative to the shoulder 230 of the hunter 102(N), and may convert that position to a wired signal 232. The wired signal 232 controls the motor 218 that displaces the earplugs 118 from the open position 202 to the closed position. While FIG. 2 illustrates the trigger mechanism 226 having first and second sensors 228(1) and 228(2) that convert the position of the butt 112 of the firearm 110 relative to the shoulder 230 of the hunter 102(N) to a wired signal 232, the first and second sensors 228(1) and 228(2) may convert the position to a wireless signal. For example, the first sensor 228(1) and/or the second sensor 228(2) may convert the position to a radio signal, an infrared signal, a Bluetooth signal, etc. that controls the motor 218 that displaces the earplugs 118 from the open position 202 to the closed position. The first and second sensors 228(1) and 228(2) may be touch sensors, electro-optical sensors, magnetic proximity sensors, etc. In an example where the first sensor 228(1) and/or the second sensor 228(2) may convert the position to a radio signal and/or a Bluetooth signal, the firearm 110 may have an accelerometer that could determine whether the firearm 110 was in a non-use position (e.g., vertical in rest position) or in a use position (e.g., horizontal in fire position). In another example where the first sensor 228(1) and/or the second sensor 228(2) may convert the position to a radio signal and/or a Bluetooth signal, the firearm 110 may have an accelerometer that senses a rapid change from a first position to a second position. Further, in another example where the first sensor 228(1) and/or the second sensor 228(2) may convert the position to a radio signal and/or a Bluetooth signal, the firearm 110 may have an accelerometer that communicates the position to the hearing protection system 114, via a device (e.g., a small computing device, a mobile device, a handheld computer, a handheld, etc.). For example, an accelerometer arranged with the firearm 110 may communicate the position of the firearm 110 to a smartphone of the user, and the smartphone may communicate the communicated position to the hearing protection system 114.

Figure 3:
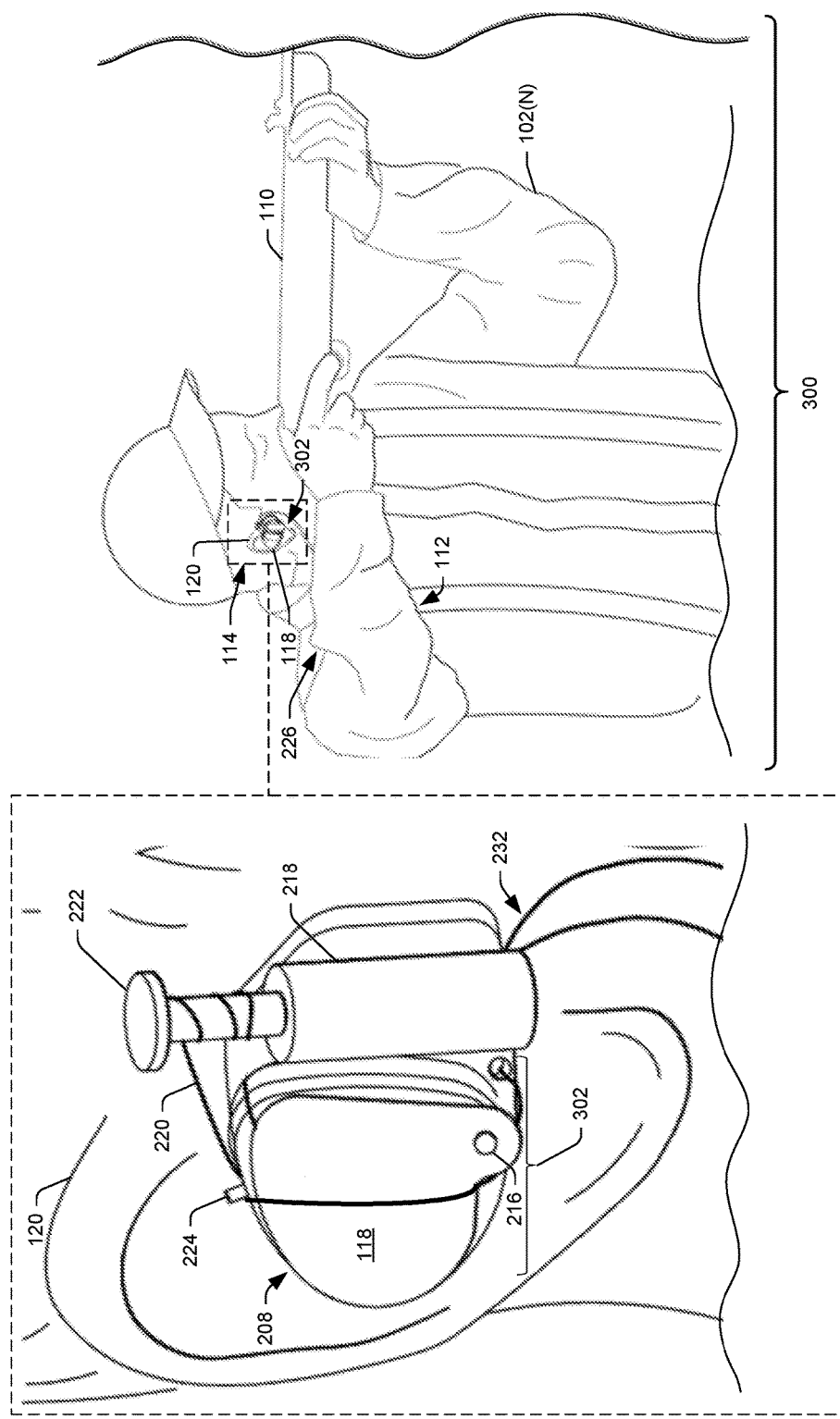
FIG. 3 illustrates a perspective view of the example hearing protection system shown in FIG. 2 in a closed position that allows the hunters shown in FIG. 1 to hear ambient sound at a reduced volume that is less than the unchanged volume.

FIG. 3 illustrates a perspective view 300 of the example hearing protection system 114 shown in FIG. 2 in a closed position 302 that allows the hunters 102(1) and 102(N) shown in FIG. 1 to hear ambient sound at a reduced volume that is less than the unchanged volume.

Detail view 304 illustrates the hearing protection system 114 in the closed position 302 in more detail, and shows the earplug 118 is positioned proximal to the ear 120 of the hunter 102(N) to at least partly block the ambient sound and allow the hunter 102(N) to hear the ambient sound at a reduced volume that is less than the unchanged volume. For example, the earplug 118 may be positioned in the ear 120 to at least partly block the ambient sound and allow the hunter 102(N) to hear the ambient sound at a reduced volume that is less than the unchanged volume. For example, when the earplug 118 is in the closed position 302, the earplug 118 may be removeably received by the cavity 210 of the receptacle 208 to at least partly seal the cavity 210 of the receptacle 208 and at least partly block the ambient sound and allow the hunter 102(N) to hear the ambient sound at the reduced volume. In another example, when the earplug 118 is in the closed position 302, the earplug 118 may be removeably received by the cavity 210 of the receptacle 208 to at least partly seal the channel 214 of the receptacle 208 and at least partly block the ambient sound and allow the user to hear the ambient sound at the reduced volume. The earplug 118 may be a cap, a flap, a plug, etc. arranged to cover the receptacle 208, or the cavity 210 of the receptacle 208. Moreover, the earplug 118 may be arranged to fit on or over the ear 120. For example, the earplug 118 may be an ear muff, an ear cup, an ear pad, etc. arranged to fit on or over the ear 120.

FIG. 3 illustrates the trigger mechanism 226 having caused the earplug 118 to displace from the open position 202 to the closed position 302 based at least in part on the position of the firearm 110 relative to the shoulder 112 the hunter 102(N). For example, FIG. 3 illustrates the first and second sensors 228(1) and 228(2) having measured the position of the butt 112 of the firearm 110 relative to the shoulder 230 of the hunter 102(N), and having converted that position to the wired signal 232. The wired signal 232 having controlled the motor 218 that displaced the earplug 118 from the open position 202 to the closed position 302. While FIG. 3 illustrates the first and second sensors 228(1) and 228(2) converting the position to the wired signal 232, the first and second sensors 228(1) and 228(2) may convert the position to a wireless signal that controls the motor 218 that displaces the earplug 118 from the open position 202 to the closed position 302.

Figure 4:
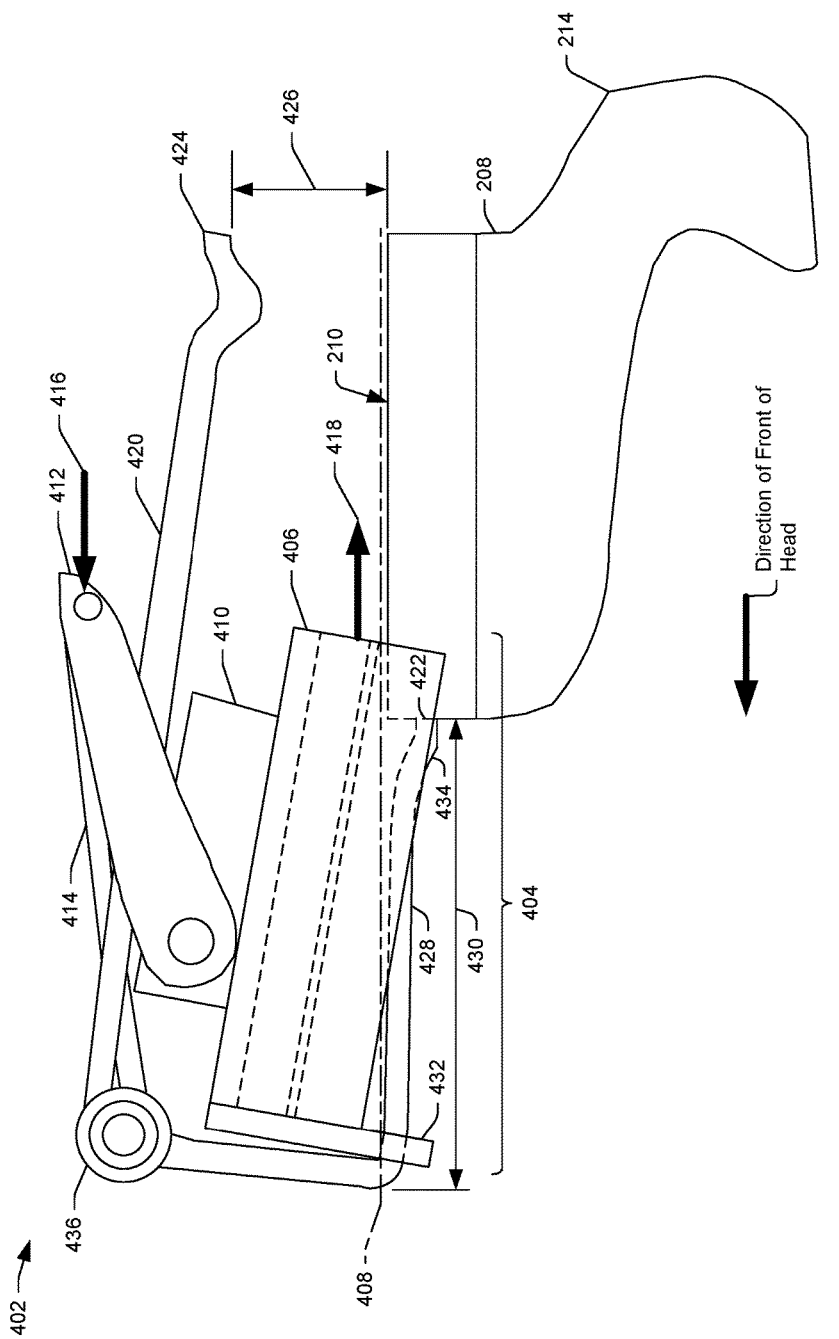
FIG. 4 illustrates a side view of another example hearing protection system in an open position that allows the hunters shown in FIG. 1 to hear ambient sound at an unchanged volume.
Figure 5:
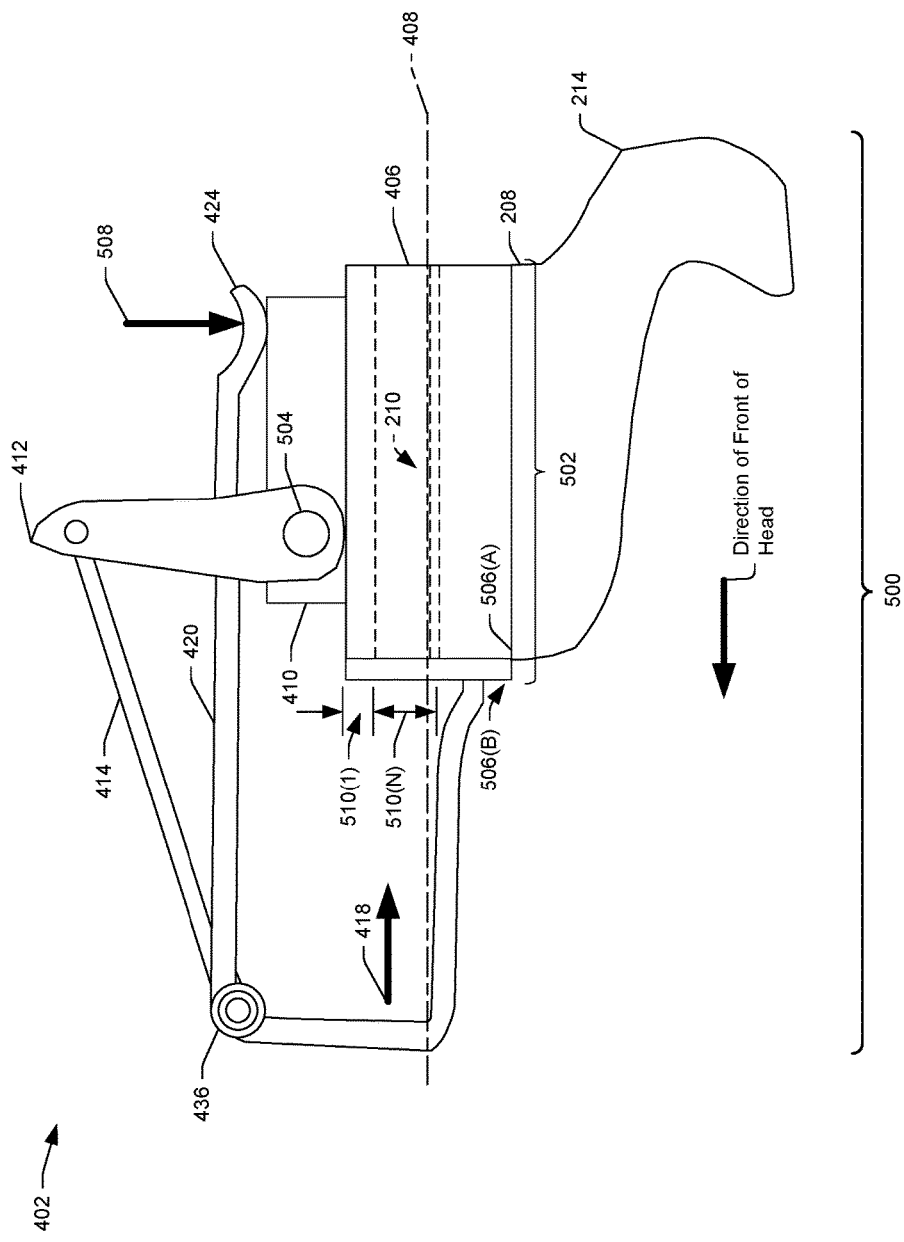
FIG. 5 illustrates a side view of the other example hearing protection system shown in FIG. 4 in a closed position that allows the hunters shown in FIG. 1 to hear ambient sound at a reduced volume that is less than the unchanged volume.

FIG. 4 illustrates a side view 400 of another example hearing protection system 402 in an open position 404 that allows the users shown in FIG. 1 to hear ambient sound at an unchanged volume, and FIG. 5 illustrates a side view 500 of the hearing protection system 402 shown in FIG. 4 in a closed position 502 that allows the hunters shown in FIG. 1 to hear ambient sound at a reduced volume that is less than the unchanged volume. Inasmuch as FIGS. 4 and 5 depict the hearing protection system 402 in the open position 404 and the closed position 502, while referring to the same elements and features of the hearing protection system 402, the following discussion of specific features may refer interchangeably to any of FIGS. 1, 2, 3, 4, and 5 except where explicitly indicated. In particular, FIGS. 4 and 5 illustrate an embodiment of the hearing protection system 402, including the receptacle 208. The receptacle 208 may be receivable by the ear 120 (illustrated in FIGS. 1, 2, and 3) and may include the cavity 210 arranged to fit in at least a portion of the ear 120. The receptacle 208 may include the channel 214 communicatively coupled to the cavity 210 and arranged to fit in at least a portion of the canal 212 of the ear 120.

Similar to the hearing protection system 114 of FIGS. 1, 2, and 3, the hearing protection system 402 is configured to protect a hearing of users (e.g., hunters 102(1) and 102(N)) from noise produced from firing a firearm (e.g., firearm 110). The actuation of the hearing protection system 402 may cause an earplug 406 of the hearing protection system 402 to be displaced from the open position 404 to the closed position 502 to protect the hearing ability of users from the noise produced from firing the firearm.

FIGS. 4 and 5 depict the earplug 406 of the hearing protection system 402 may be moveably disposed in a plane 408 covering the cavity 210 of the receptacle 208. The earplug 406 may moveably displace in the plane 408 between the open position 404 and the closed position 502. FIG. 4 illustrates that when the earplug 406 is in the open position 404, the earplug 406 is positioned adjacent to the cavity 210 of the receptacle 208 to allow the user to hear ambient sound at an unchanged volume. FIG. 5 illustrates that when the earplug 406 is in the closed position 502, the earplug 406 is positioned over the cavity 210 of the receptacle 208 to at least partly block the ambient sound and allow the user to hear the ambient sound at a reduced volume that is less than the unchanged volume.

FIG. 4 depicts the hearing protection system 402 may include a servomechanism 410. The servomechanism 410 may be attached to the earplug 406. In one example, the servomechanism 410 may be attached to a top surface of the earplug 406. In another example, the servomechanism 410 may be attached to a side surface of the earplug 406. In another example, the servomechanism 410 may be attached to an inside surface of the earplug 406. In another example, the servomechanism 410 may be attached to the receptacle 208.

An arm 412 of the servomechanism 410 may be pivotably attached to a link 414. For example, the arm 412 of the servomechanism 410 may be pivotably attached to the link 414 via a bail or torque bail (explained in more detail below with regard to FIG. 6). The arm 412 of the servomechanism 410 may apply a force in a direction 416 to a portion of the link 414 to cause the earplug 406 to be displaced in a direction 418, from the open position 404, to the closed position 502 when the servomechanism 410 is actuated.

FIG. 4 depicts the link 414 may be pivotably attached to a structural member 420. The structural member 420 may attach to a portion of the receptacle 208. The structural member 420 may be an elongated member (e.g., a wire, a spring wire, a rod, etc.) attached to the portion of the receptacle 208. For example, the structural member 420 may be a spring wire having a first end 422 attached to the receptacle 208 and a second end 424 arranged a distance 426 above the receptacle 208. The structural member 420 may include a guide portion 428 extending a distance 430 from the receptacle 208. The guide portion 428 of the structural member 420 may provide a guide (e.g., a rail, a beam, a support, etc.) for the earplug 406 when the earplug 406 is moveably displaced. For example, the earplug 406 may include a follower 432 attached to the earplug 406 that may be guided by the guide portion 428 of the structural member 420 when the earplug 406 is moveably displaced. For example, the follower 432 may be linearly guided along the guide portion 428 of the structural member such that the earplug 406 is linearly displaced in the plane 408 covering the cavity 210 of the receptacle 208. The guide portion 428 may have a bend 434 arranged proximate to the receptacle 208. The bend 434 may provide for the guide portion 428 to guide the earplug 406 to a position on a surface of the receptacle 208 as the earplug 406 is displaced the direction 418 from the open position 404 to the closed position 502 when the servomechanism 410 is actuated.

FIG. 4 depicts the structural member 420 may include an attachment portion 436 arranged a distance from the guide portion 428. The attachment portion 436 may provide for pivotably attaching an end of the link 414 opposite the portion of the link 414 pivotably attached to the arm 412 of the servomechanism 410 via the bail or torque bail. The attachment portion 436 of the structural member 420 may comprise an opening formed in the structural member 420. For example, the structural member 420 may be an elongated member (e.g., a wire, a spring wire, a rod, etc.) and the opening may be formed of a winded portion (e.g., a coil, a twist, a loop, etc.) of the elongated member. The winding may be formed of about a 450 degree winding of the elongated member. The winding of the structural member 420 may also provide at least an amount of spring force to the second end 424 of the structural member 420 for applying a force in a direction orthogonal to the plane 408 to force the earplug 406 onto the receptacle 208 and at least partially close or at least partially seal (e.g., air tight seal) the cavity 210 of the receptacle 208 (explained in more detail below with regard to FIG. 5).

Similar to the hearing protection system 114, the hearing protection system 402 may use a trigger mechanism, responsive to movement of the firearm 110, to cause the earplugs to displace between the open position 404 and the closed position 502 based at least in part on a position of the firearm 110. For example, the trigger mechanism may include a wireless trigger mechanism attached to a device (e.g., firearm 110), the wireless trigger mechanism to monitor an orientation of the device to cause the earplug 406 to displace between the open position 404 and the closed position 502. The wireless trigger mechanism may comprise a wireless gyroscope and/or accelerometer trigger arranged with the device that causes the earplug 406 to displace between the open position 404 and the closed position 502 based at least in part on the position of the device. For example, a wireless gyroscope and/or accelerometer trigger may be arranged with a handgun (e.g., a pistol, a revolver, etc.) that detects an orientation of the handgun in response to the barrel of the handgun extending in a direction that is within about 30 degrees of horizontal. When the wireless gyroscope and/or accelerometer trigger detects an orientation of the handgun being at the position within about 30 degrees of horizontal, the earplug 406 may be caused to be displaced to the closed position 502. When the wireless gyroscope and/or accelerometer trigger detects an orientation of the handgun being a position other than the position within about 30 degrees of horizontal, the earplug may be caused to be displaced to the open position 404. In some examples, the gyroscope of the gyroscope and/or accelerometer trigger may provide a relationship of the handgun to the world absolutely, while the accelerometer of the gyroscope and/or accelerometer trigger may provide how fast the handgun is moving away from the relationship. Because the gyroscope of the gyroscope and/or accelerometer trigger may drift, the gyroscope and/or accelerometer trigger may use both of the gyroscope and the accelerometer together to counteract the drift of the gyroscope.

Similar to the hearing protection systems 114, the wireless interconnection interconnecting the hearing protection systems 402 may be a radio interconnection, an infrared interconnection, a Bluetooth interconnection, etc. The wireless trigger mechanism may be any device that measures the position of a device, and converts that position to a wireless signal that controls the servomechanism 410 that displaces the earplugs 406 from the open position 404 to the closed position 502, or vice versa. Further, the wireless trigger mechanism may be a biometric trigger mechanism that controls the servomechanism 410 that displaces the earplugs 406 from the open position 404 to the closed position 502, or vice versa. For example, the wireless trigger mechanism may be a biometric trigger mechanism that operates on biofeedback of the user. For example, the wireless trigger mechanism may be a biometric mechanism arranged with eye protection (e.g., safety glasses, glasses, safety goggles, goggles, etc.) that operates on biofeedback of an eye of a user. For example, the biometric mechanism arranged with eye protection may cause the servomechanism 410 to displace the earplugs 406 from the open position 404 to the closed position 502 when a left eye of a user is closed (e.g., blinked), and cause the servomechanism 410 to displace the earplugs 406 from the closed position 502 to the open position 404 when a right eye of a user is closed (e.g., blinked), or vice versa. In another example, the biometric mechanism may be voice activated and may cause the servomechanism 410 to displace the earplugs 406 between the open position 404 and the closed position 502 when a user makes an utterance.

FIG. 5 depicts the hearing protection system 402 in the closed position 502 where the earplug 406 is positioned over the cavity 210 of the receptacle 208 to at least partly block the ambient sound and allow the user to hear the ambient sound at a reduced volume that is less than the unchanged volume. FIG. 5 depicts the arm 412 of the servomechanism 410 may rotate counterclockwise relative to a shaft 504 of the servomechanism 410 to cause the earplug 406 to be displaced in the direction 418 to the closed position 502. To displace the earplug 406 to the open position 404 illustrated in FIG. 4, the arm 412 of the servomechanism 410 may rotate clockwise relative to the shaft 504 of the servomechanism 410 to cause the earplug 406 to be displaced in the opposite direction of the direction 418 to the open position 404.

FIG. 5 depicts the earplug 406 may include one or more guide rails 506(A) and 506(B). The one or more guide rails 506(A) and 506(B) (also shown in FIG. 6) may provide for guiding the earplug 406 over the receptacle 208. For example, the one or more guide rails 506(A) and 506(B) may cooperate with an outside surface of the receptacle 208 to slideably guide the earplug 406 linearly over the receptacle 208 such that the earplug 406 is linearly displaced in the plane 408 covering the cavity 210 of the receptacle 208.

Further, FIG. 5 depicts the second end 424 of the structural member 420 may be shifted from a free position to a contact position against the servomechanism 410 as the servomechanism 410 is displaced under the second end 424 of the structural member 420. For example, as the arm 412 of the servomechanism 410 rotates counterclockwise to cause the earplug 406 to be displaced in the direction 418 to the closed position 502, the second end 424 of the structural member 420 may be displaced from the free position by the sliding insertion of the servomechanism 410 between the structural member 420 and the receptacle 208. The second end 424 of the structural member 420 may apply a force in a direction 508 orthogonal to the plane 408 covering the cavity 210 of the receptacle 208 to at least partially close or at least partially seal (e.g., air tight seal) the cavity 210 of the receptacle 208 and at least partly block the ambient sound and allow the user to hear the ambient sound at the reduced volume. The attachment portion 436 of the structural member 420 may provide at least an amount of spring force or biasing force to the second end 424 of the structural member 420. For example, the attachment portion 436 may be formed of a winding (e.g., a coil, a twist, a loop, etc.) that may provide at least an amount of spring force to the second end 424 of the structural member 420. The winding of the attachment portion 436 may provide for applying the force in the direction 508 orthogonal to the plane 408. The force applied in the direction 508 may force the earplug 406 onto the receptacle 208 and at least partially close or at least partially seal (e.g., air tight seal) the cavity 210 of the receptacle 208 and at least partly block the ambient sound and allow the user to hear the ambient sound at the reduced volume (explained in more detail below with regard to FIG. 5). Further, the second end 424 of the structural member 420 may apply the force in the direction 508 orthogonal to the plane 408 covering the cavity 210 of the receptacle 208 as a result of the second end 424 of the structural member 420 being displaced a distance greater than the distance 426. For example, when the second end 424 of the structural member 420 is displaced a distance greater than the distance 426, the winding or spring of the attachment portion 436 may be displaced (e.g., stretched) from the springs resting position and provide at least an amount of spring force to the second end 424 of the structural member 420 to apply the force in the direction 508.

The second end 424 of the structural member 420 may have a curved portion (e.g., a hook, a bend, a bump, etc.) that may apply the force in the direction 508 orthogonal to the plane 408 covering the cavity 210 of the receptacle 208 to at least partially close or at least partially seal (e.g., air tight seal) the cavity 210 of the receptacle 208 and at least partly block the ambient sound and allow the user to hear the ambient sound at the reduced volume. In some examples, when the arm 412 of the servomechanism 410 has completed the rotation counterclockwise to cause the earplug 406 to be in the closed position 502, the arm 412 may apply a force in the direction 508 orthogonal to the plane 408 to at least partially close or at least partially seal (e.g., air tight seal) the cavity 210 of the receptacle 208 and at least partly block the ambient sound and allow the user to hear the ambient sound at the reduced volume.

FIG. 5 depicts the earplug 406 may include one or more layers 510(1) and 510(N) of material arranged adjacent to each. Each of the one or more layers 510(1) and 510(N) may be formed of a material having a different density. For example, the layer 510(1) may be formed of a first material having a first density, and the layer 510(N) may be formed of a second material having a second density different from the first density of the first material. In one example, the layer 510(1) may be formed of a composite (e.g., a wood composite, a plywood, a modeling plywood, a fiberglass, a carbon fiber reinforced polymer, etc.), and the layer 510(N) may be formed of a plastic (e.g., polyethylene (PE), polypropylene (PP), polystyrene (PS), polyamides (PA), polyurethanes (PU), silicon, etc.). In another example, the layers 510(1) and 510(N) may each be formed of a plastic.

The layer 510(1) may be formed of a material having a density greater than a density of a material forming the layer 510(N). For example, the layer 510(1) may be formed of a material having a greater density than the density of the material forming the layer 510(N) to provide for mounting the servomechanism 410 to the layer 510(1). Moreover, the layer 510(N) may be formed of a material having a lesser density than the density of the material forming the layer 510(1) to provide for at least partially sealing (e.g., air tight seal) the earplug 406 to the cavity 210 of the receptacle 208. For example, the layer 510(N) may be formed of a silicon (e.g., a low durometer silicone) to provide for at least partially sealing (e.g., air tight seal) the earplug 406 to the cavity 210 of the receptacle 208. For example, the second end 424 of the structural member 420 may apply the force in the direction 508 orthogonal to the plane 408 covering the cavity 210 of the receptacle 208 to compress the layer 510(N) formed of a low durometer material between the first layer 510(1) and the receptacle 208 to at least partially close or at least partially seal (e.g., air tight seal) the cavity 210 of the receptacle 208 and at least partly block the ambient sound and allow the user to hear the ambient sound at the reduced volume. While FIG. 5 illustrates the earplug 406 comprising two layers, the earplug 406 may comprise fewer than two layers or may comprise more than two layers. The one or more layers 510(1) and 510(N) may have a total thickness that provides for at least partly blocking the ambient sound and allow the user to hear the ambient sound at the reduced volume.

Figure 6:
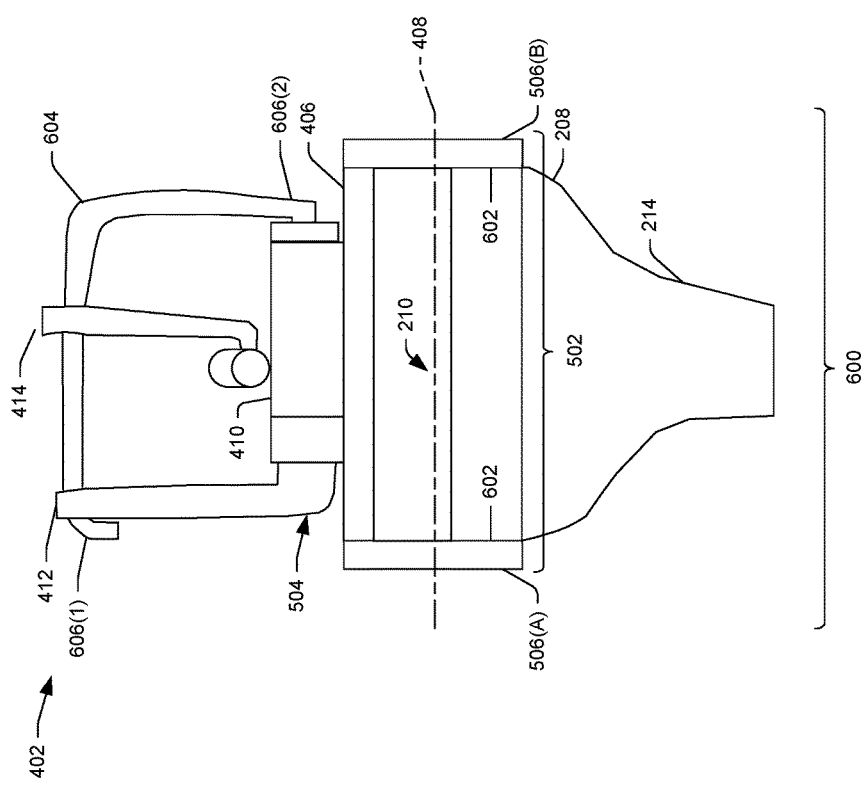
FIG. 6 illustrates a back view of the other example hearing protection system shown in FIG. 5 in the closed position.

FIG. 6 illustrates a back view 600 of the hearing protection system 402 shown in FIG. 5 in the closed position 502 that allows the hunters shown in FIG. 1 to hear ambient sound at a reduced volume that is less than the unchanged volume. FIG. 6 depicts the one or more guide rails 506(A) and 506(B) as cooperating with the outside surface 602 of the receptacle 208 to slideably guide the earplug 406 linearly over the receptacle 208 such that the earplug 406 is linearly displaced in the plane 408 covering the cavity 210 of the receptacle 208.

FIG. 6 also depicts that the arm 412 of the servomechanism 410 may be pivotably attached to the link 414 via a bail 604 (e.g., torque bail). A first end 606(1) of the bail 604 may be pivotably attached to the arm 412 of the servomechanism 410 and a second end 606(2) of the bail 604 may be pivotably attached to a portion of the earplug 406. For example, the first end 606(1) of the bail 604 may be pivotably attached to an end of the arm 412 and the second end 606(2) of the bail 604 may be pivotably attached to the servomechanism 410. FIG. 6 depicts the link 414 pivotably attached to the bail 604. For example, the link 414 may be pivotably attached to a portion of the bail 604 arranged between the first end 606(1) and the second end 606(2) of the bail 604. Thus, when the servomechanism 410 is actuated by a trigger mechanism to cause the earplug 406 to be displaced from the open position 404 to the closed position 502, the arm 412 of the servomechanism 410 may rotate counterclockwise relative to the shaft 504 of the servomechanism 410 and apply a force in the direction 416 to the portion of the link 414 via the bail 604 to cause the earplug 406 to be displaced from the open position 404 to the closed position 502. Further, when the servomechanism 410 is actuated by a trigger mechanism to cause the earplug 406 to be displaced from the closed position 502 to the open position 404, the arm 412 of the servomechanism 410 may rotate clockwise relative to the shaft 504 of the servomechanism 410 and apply a force in a direction opposite the direction 416 to the portion of the link 414 via the bail 604 to cause the earplug 406 to be displaced from the closed position 502 to the open position 404.

Figure 7:
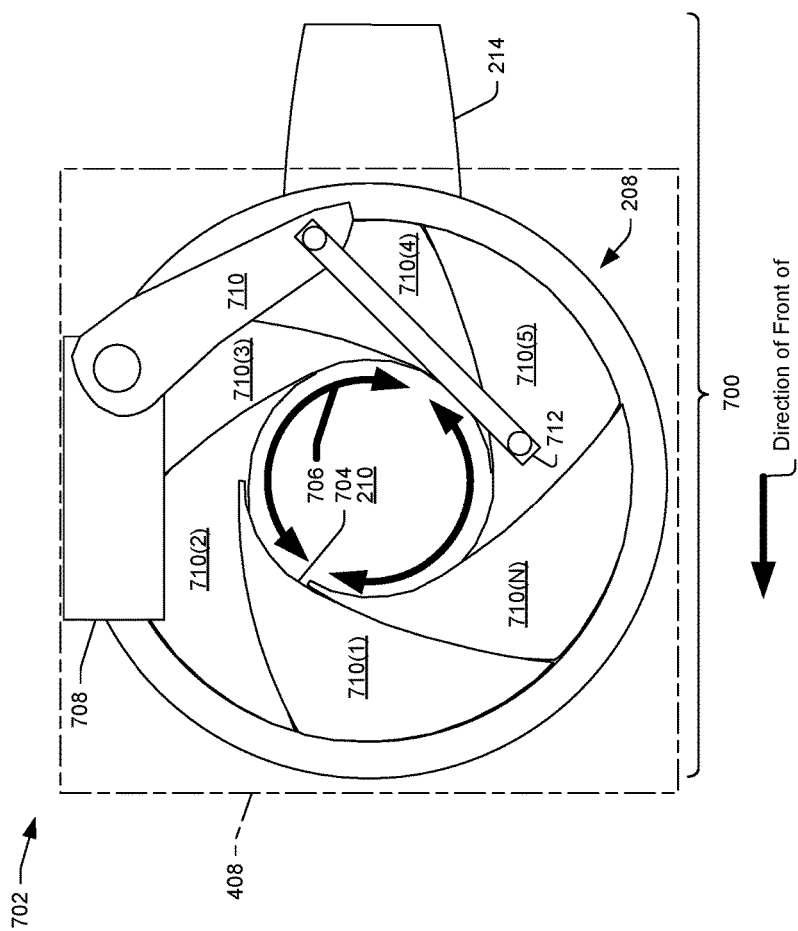
FIG. 7 illustrates a top view of another example hearing protection system.

FIG. 7 illustrates a top view 700 of another example hearing protection system 702. The hearing protection systems 702 may include an earplug 704 displaceable between an open position and a closed position. For example, the earplug 704 may be displaced from the open position, where the earplug 704 is positioned such that cavity 210 is exposed to the atmosphere to allow the user to hear ambient sound at an unchanged volume, to the closed position 502, where the earplug 704 is positioned such that the cavity is closed off from the atmosphere to at least partly block the ambient sound and allow the user to hear the ambient sound at a reduced volume that is less than the unchanged volume.

Inasmuch as FIG. 7 depicts the hearing protection system 702 being displaceable between the open position 404 and the closed position 502, while referring to the same elements and features of the hearing protection system 702, the following discussion of specific features may refer interchangeably to any of FIGS. 1, 2, 3, 4, 5, and 6 except where explicitly indicated. In particular, FIG. 7 illustrates an embodiment of the hearing protection system 702, including the receptacle 208. The receptacle 208 may be receivable by the ear 120 (illustrated in FIGS. 1, 2, and 3) and may include the cavity 210 arranged to fit in at least a portion of the ear 120. The receptacle 208 may include the channel 214 communicatively coupled to the cavity 210 and arranged to fit in at least a portion of the canal 212 of the ear 120.

Similar to the hearing protection systems 114 of FIGS. 1, 2, 3, and the hearing protection systems 402 of FIGS. 4, 5, and 6, the hearing protection system 702, is configured to protect a hearing of users (e.g., a hunters 102(1) and 102(N)) from noise produced from firing a firearm (e.g., firearm 110). The actuation of the hearing protection system 702 may cause the earplug 704 of the hearing protection system 702 to be displaced from the open position 404 to the closed position 502 to protect the hearing abilities of users from the noise produced from firing the firearm.

FIG. 7 depicts the earplug 704 of the hearing protection system 702 may be moveably disposed in the plane 408 covering the cavity 210 of the receptacle 208. The earplug 704 may moveably displace in the plane 408 between the open position 404 and the closed position 502. FIG. 7 illustrates that when the earplug 704 is moveably displaced in the plane 408 between the open position 404 and the closed position 502, the earplug 704 may be moveably displaced radially 706 in the plane 408 above the cavity 210 of the receptacle 208 between the open position 404 and the closed position 502.

FIG. 7 depicts the hearing protection system 702 may include a servomechanism 708. The servomechanism 708 may be attached to the earplug 704. In one example, the servomechanism 708 may be attached to a top surface of the earplug 704. In another example, the servomechanism 708 may be attached to a side surface of the earplug 704. In another example, the servomechanism 708 may be attached to the receptacle 208.

An arm 710 of the servomechanism 708 may be pivotably attached to a link 712. The arm 710 of the servomechanism 708 may apply a force in a direction to a portion of the link 712 to cause the earplug 704 to be displaced radially 706, from the open position 404, to the closed position 502 when the servomechanism 708 is actuated.

Similar to the hearing protection systems 114 and 402, the hearing protection system 702 may use a trigger mechanism, responsive to movement of the firearm 110, to cause the earplugs to displace between the open position 404 and the closed position 502 based at least in part on a position of the firearm 110. Further, the wireless trigger mechanism may comprise a wireless gyroscope and/or accelerometer trigger arranged with the device that causes the earplug 704 to displace between the open position 404 and the closed position 502 based at least in part on the position of the device.

Similar to the hearing protection systems 114 and 402, the wireless interconnection interconnecting the hearing protection systems 702 may be a radio interconnection, an infrared interconnection, a Bluetooth interconnection, etc. The wireless trigger mechanism may be any device that measures the position of a device, and converts that position to a wireless signal that controls the servomechanism 708 that displaces the earplugs 704 from the open position 404 to the closed position 502, or vice versa. Further, the wireless trigger mechanism may be a biometric trigger mechanism that controls the servomechanism 708 that displaces the earplugs 704 from the open position 404 to the closed position 502, or vice versa.

FIG. 7 depicts the earplug 704 may include one or more pivoting members 714(1), 714(2), 714(3), 714(4), 714(5), and 714(N). Similar to the hearing protection systems 402, each of the one or more pivoting members 714(1)-714(N) of the earplug 704 may include one or more layers (e.g., one or more layers 510(1) and 510(N)) formed of a material having a different density. In another example, each of the one or more pivoting members 714(1)-714(N) of the earplug 704 may include a single layer of material. In one example, the one or more layers of each of the one or more pivoting members 714(1)-714(N) may have a total thickness that provides for at least partly blocking the ambient sound and allow the user to hear the ambient sound at the reduced volume. In another example, the one or more layers of each of the one or more pivoting members 714(1)-714(N) may have a thickness that is a fraction of a total thickness that provides for at least partly blocking the ambient sound and allowing the user to hear the ambient sound at the reduced volume.

CONCLUSION

Although the invention has been described in language specific to structural features and/or methodological acts, it is to be understood that the invention is not necessarily limited to the specific features or acts described. Rather, the specific features and acts are disclosed as illustrative forms of implementing the invention. For example, while embodiments are described having certain shapes, sizes, and configurations, these shapes, sizes, and configurations are merely illustrative.

What is claimed is:

1. A hearing protection system comprising:
   a hollow earpiece arrangeable in an ear of a first user, the hollow earpiece including a cavity that interfaces with an inside of the ear proximate to an opening of a canal of the ear;
   a structural member attached to the hollow earpiece;
   an earplug slideably attached to the structural member such that the earplug is slideably disposed linearly in a plane covering the cavity of the hollow earpiece, the earplug to slideably displace in the plane between an open position and a closed position;
   a servomechanism attached to the earplug;
   a wireless trigger mechanism to monitor an orientation of a firearm operated by a second user and to protect a hearing of the first user from a noise produced from the second user firing the firearm,
   wherein the wireless trigger mechanism controls the servomechanism to cause the servomechanism to displace the earplug between the open position and the closed position based at least in part on an indication of the orientation of the firearm received from the wireless trigger mechanism, and
   wherein:
      when in the open position, the earplug is positioned adjacent to the cavity of the hollow earpiece to allow the first user to hear ambient sound at an unchanged volume, and
      when in the closed position, the earplug is positioned over the cavity of the hollow earpiece and forced, via the structural member, in a direction orthogonal to the plane and onto the hollow earpiece to at least partly block the ambient sound and allow the first user to hear the ambient sound at a reduced volume that is less than the unchanged volume.

2. The hearing protection system of claim 1, further comprising a biometric trigger mechanism to cause the earplug to displace between the open position and the closed position.

3. The hearing protection system of claim 1, wherein the firearm comprises a long gun or a handgun.

4. A hearing protection system comprising:
   a hollow earpiece arranged to fit in at least a portion of an ear of a first user, the hollow earpiece including a cavity arranged to interface with an inside of the ear proximate to an opening of an auditory canal of the ear;
   a structural member attached to the hollow earpiece;
   an earplug slideably attached to the structural member such that the earplug is slideably disposed linearly in a plane covering the cavity of the hollow earpiece from an open position to a closed position in response to a wireless signal received from a wireless trigger mechanism;
   a servomechanism attached to the earplug,
   wherein the wireless trigger mechanism monitors an orientation of a firearm operated by a second user and protects a hearing of the first user from a noise produced from the second user firing the firearm, the wireless trigger mechanism to control the servomechanism to cause the servomechanism to displace the earplug between the open position and the closed position based at least in part on an indication of the orientation of the firearm received from the wireless trigger mechanism, and
   wherein when in the open position, the earplug is positioned adjacent to the cavity of the hollow earpiece to allow the first user to hear ambient sound at an unchanged volume, and when in the closed position, the earplug is positioned over the cavity of the hollow earpiece and forced, via the structural member, in a direction orthogonal to the plane and onto the hollow earpiece to at least partly block the ambient sound and allow the first user to hear the ambient sound at a reduced volume that is less than the unchanged volume.

5. The hearing protection system of claim 4, further comprising a biometric trigger mechanism to cause the earplug to displace between the open position and the closed position.

6. The hearing protection system of claim 4, wherein the firearm comprises a long gun or a handgun.

7. A hearing protection system comprising:
   a first hearing protection system for a first user and a second hearing protection system for a second user;
   the first hearing protection system including:
      a first hollow earpiece arrangeable in a first ear of the first user, the first hollow earpiece including a cavity that interfaces with an inside of the first ear proximate to an opening of a canal of the first ear;

a first structural member attached to the first hollow earpiece;

a first earplug slideably attached to the first structural member such that the first earplug is slideably disposed linearly in a plane covering the cavity of the first hollow earpiece, the first earplug to slideably displace in the plane between an open position and a closed position;

a first servomechanism attached to the first earplug;

a first wireless trigger mechanism associated with the first user, the first wireless trigger mechanism to monitor an orientation of a first firearm operated by the first user and to protect a hearing of the first user and a hearing of the second user from a noise produced from the first user firing the firearm; and the second hearing protection system including:

a second hollow earpiece arrangeable in a second ear of the second user, the second hollow earpiece including a cavity that interfaces with an inside of the second ear proximate to an opening of a canal of the second ear;

a second structural member attached to the second hollow earpiece;

a second earplug slideably attached to the second structural member such that the second earplug is slideably disposed linearly in a plane covering the cavity of the second hollow earpiece, the second earplug to slideably displace in the plane between the open position and the closed position;

a second servomechanism attached to the second earplug;

a second wireless trigger mechanism associated with the second user, the second wireless trigger mechanism to monitor an orientation of a second firearm operated by the second user and to protect a hearing of the first user and a hearing of the second user from a noise produced from the second user firing the firearm;

wherein each of the first wireless trigger mechanism and the second wireless trigger mechanism control the first servomechanism and the second servomechanism respectively to cause the first servomechanism and the second servomechanism to displace each of the first earplug and the second earplug respectively between the open position and the closed position based at least in part on an indication of the orientation of the first firearm or the orientation of the second firearm received from the first wireless trigger mechanism or the second wireless trigger mechanism, and wherein:

when in the open position, the first earplug is positioned adjacent to the cavity of the first hollow earpiece to allow the first user to hear ambient sound at an unchanged volume, and the second earplug is positioned adjacent to the cavity of the second hollow earpiece to allow the second user to hear ambient sound at an unchanged volume, and when in the closed position, the first earplug is positioned over the cavity of the first hollow earpiece and forced, via the first structural member, in a direction orthogonal to the plane and onto the first hollow earpiece to at least partly block the ambient sound and allow the first user to hear the ambient sound at a reduced volume that is less than the unchanged volume, and the second earplug is positioned over the cavity of the second hollow earpiece and forced, via the second structural member, in a direction orthogonal to the plane and onto the second hollow earpiece to at least partly block the ambient sound and allow the second user to hear the ambient sound at a reduced volume that is less than the unchanged volume.

* * * * *